US009791429B2

(12) United States Patent
Howes, Jr. et al.

(10) Patent No.: US 9,791,429 B2
(45) Date of Patent: Oct. 17, 2017

(54) SENSOR SYSTEM AND METHOD FOR SENSING CHLORINE CONCENTRATION

(71) Applicant: Ecolab USA Inc., St. Paul, MN (US)

(72) Inventors: Ronald Bruce Howes, Jr., Minneapolis, MN (US); Patrick Henry Kilawee, Hugo, MN (US); Michael Patrick Kremer, Rosemount, MN (US); Leonard John Kadlec, Woodbury, MN (US)

(73) Assignee: Ecolab USA Inc., Saint Paul, MN (US)

( * ) Notice: Subject to any disclaimer, the term of this patent is extended or adjusted under 35 U.S.C. 154(b) by 244 days.

(21) Appl. No.: 14/533,343

(22) Filed: Nov. 5, 2014

(65) Prior Publication Data
US 2016/0123950 A1 May 5, 2016

(51) Int. Cl.
G01N 33/18 (2006.01)
G01N 1/20 (2006.01)
G01N 1/10 (2006.01)
G01N 1/22 (2006.01)

(52) U.S. Cl.
CPC ....... *G01N 33/1813* (2013.01); *G01N 1/2035* (2013.01); *G01N 2001/1062* (2013.01); *G01N 2001/2285* (2013.01)

(58) Field of Classification Search
CPC ....... G01N 33/1813; G01N 2001/2285; G01N 2001/1062; G01N 1/2035
See application file for complete search history.

(56) References Cited

U.S. PATENT DOCUMENTS

| 2,851,655 A | 9/1958 | Haddad |
| 3,959,087 A | 5/1976 | Morrow |
| 4,033,830 A | 7/1977 | Fletcher, III |
| 4,129,479 A | 12/1978 | Morrow |
| 4,822,474 A | 4/1989 | Corrado |

(Continued)

FOREIGN PATENT DOCUMENTS

| DE | 10029568 A1 | 7/2003 |
| EP | 0065166 A2 | 11/1982 |

(Continued)

OTHER PUBLICATIONS

International Search Report and Written Opinion for PCT/US2015/057734, Date of Mailing: Feb. 7, 2016, 18 pages.

(Continued)

*Primary Examiner* — Blake A Tankersley
*Assistant Examiner* — Quang X Nguyen
(74) *Attorney, Agent, or Firm* — Fredrikson & Byron, P.A.

(57) ABSTRACT

Certain embodiments include a sensor system for measuring chlorine concentration in water. The sensor system can have a manifold including one or more flow passages for receiving fluid flow. The sensor system can have a probe for measuring chlorine concentration in fluid communication with a flow passage of the one or more flow passages of the manifold. The probe can have a probe body oriented to direct incoming fluid from one or more flow passages of the manifold toward an end of the probe body. The probe can have a plurality of flutes defined on an outer surface of the probe body. The flutes can be shaped and oriented to direct fluid from the end proximal to the electrodes, back toward the one or more flow passages of the manifold.

17 Claims, 8 Drawing Sheets

(56) References Cited

U.S. PATENT DOCUMENTS

| | | | |
|---|---|---|---|
| 5,230,785 A * | 7/1993 | Yager | G01N 33/182 204/400 |
| 6,338,782 B1 | 1/2002 | Imamura et al. | |
| 7,100,427 B2 * | 9/2006 | Kahn | G01N 33/18 73/53.01 |
| 8,505,565 B2 | 8/2013 | Hin et al. | |
| 2001/0042692 A1 | 11/2001 | Gurry et al. | |
| 2003/0033848 A1 | 2/2003 | Peng | |
| 2004/0211731 A1 | 10/2004 | Ferguson et al. | |
| 2007/0158274 A1 | 7/2007 | King | |
| 2009/0201032 A1 | 8/2009 | Burdett et al. | |
| 2011/0308645 A1 | 12/2011 | Thai et al. | |
| 2013/0036799 A1 * | 2/2013 | Silveri | G01N 27/4168 73/61.41 |
| 2013/0233728 A1 | 9/2013 | Day et al. | |
| 2014/0026971 A1 | 1/2014 | Roach et al. | |
| 2014/0326680 A1 | 11/2014 | Mastio | |

FOREIGN PATENT DOCUMENTS

| | | |
|---|---|---|
| EP | 0065167 A2 | 11/1982 |
| FR | 2947634 A1 | 1/2011 |
| JP | 2007117882 A | 5/2007 |
| MX | 2009010771 A | 4/2011 |
| WO | 9924369 A2 | 5/1999 |
| WO | 0238507 A1 | 5/2002 |
| WO | 2011003923 A1 | 1/2011 |
| WO | 2012112611 A2 | 8/2012 |

OTHER PUBLICATIONS

U.S. Appl. No. 14/535,523, entitled: "PPM Pool Sensor," filed Nov. 7, 2014, 30 pages.

International Search Report for PCT/US2015/057741, Date of Mailing: Feb. 10, 2016, 10 pages.

* cited by examiner

SENSOR SYSTEM AND METHOD FOR SENSING CHLORINE CONCENTRATION

FIELD

This disclosure generally relates to systems and methods for measuring concentration of certain substances in a fluid. More particularly, this disclosure relates to systems and methods for measuring chlorine concentration.

BACKGROUND

Dispensing systems for dosing certain substances (e.g., chlorine) in fluids (e.g., recreational water bodies such as pools, spas, water parks, and the like) often require sensing the concentration of the substance. One type of sensor for such applications is an Oxidation-Reduction Potential (ORP) sensor for monitoring levels of chlorine in recreational water bodies. ORP sensors measure the ability of a substance to act as an oxidizing or reducing agent. Chlorine is an oxidizing agent, and the presence of chlorine in fluids can therefore be indirectly measured by the ORP sensor. ORP sensors are widely used due to their lower cost. However, ORP sensors may have several disadvantages. For instance, ORP sensors can have a non-linear signal response to chlorine concentration in the range of chlorine concentrations typically used in recreational water bodies (e.g., 1 to 10 ppm). Also, high levels of impedance characteristics of ORP sensors may result in leakage current errors and stray electrical noise pickup, thereby reducing the accuracy of measurement. Moreover, ORP sensors typically do not directly sense chlorine concentration and rather sense oxidation reduction potential, which in turn is affected by pH, temperature, and the presence of other chemical species in the fluid. As a result, ORP sensors may need a calibration procedure to measure the ORP sensor response to chlorine concentration in a given water body. ORP sensors therefore must be "hand tuned" according to the physical conditions (e.g., pH, temperature, etc.) prevalent in each water body where ORP sensors are used. Such calibration procedures can become unreliable over time due to changing conditions in the water body and may increase equipment and maintenance costs.

Another type of sensor for measuring concentration of certain substances (e.g., chlorine) in a fluid (e.g., water) is an amperometric sensor. Such amperometric sensors can measure concentration of an ion based on an electric current (or changes therein) flowing between a pair of electrodes. Unlike ORP sensors, amperometric sensors can have a linear signal response to chlorine concentration and low electrical impedance. As a result, there may not be significant electrical noise interference in amperometric sensors resulting better accuracy of measurement than ORP sensors. Such sensors also have a simple construction and low cost due to sensor response being predictable across different sensors eliminating the need for high cost calibration procedures.

SUMMARY OF THE INVENTION

Certain embodiments of the invention include a sensor system for measuring chlorine concentration in water. The sensor system can have a manifold including one or more flow passages for receiving fluid flow. The sensor system can include sensors in fluid communication with the one or more flow passages of the manifold to measure one or more fluid properties of the fluid flowing through the one or more flow passages of the manifold. The sensor system can include a probe for measuring chlorine concentration. The probe can be positioned in fluid communication with a flow passage of the one or more flow passages of the manifold. The probe can have a probe body for housing a plurality of electrodes. The electrodes can generate a current in response to the concentration of chlorine present in the fluid. The probe body can be oriented to direct incoming fluid from one or more flow passages of the manifold toward an end proximal to the electrodes.

In some embodiments, the probe body can have a hollow portion in fluid communication with a flow passage of the manifold. In some cases, a nozzle can be in fluid communication with the hollow portion of the probe body. The nozzle can be coaxial with the hollow portion of the probe body thereby defining an annulus therebetween and a flow passage of the manifold. The nozzle can receive fluid from the hollow portion. The nozzle can be shaped to direct the fluid from the hollow portion toward the second end. In some embodiments, the probe can have a plurality of flutes defined on an outer surface of the probe body. The flutes can be shaped and oriented to direct fluid from the end proximal to the electrodes, back toward the one or more flow passages of the manifold.

BRIEF DESCRIPTION OF DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention provide a sensor system 100 with an amperometric sensor for measuring concentration of certain substances (e.g., chlorine) in a fluid (e.g., water). The sensor system 100 can optionally include one or more sensors for measuring fluid properties such as pH, temperature, concentration, flow rate of fluid through the sensor system, and the like. Such amperometric sensors can be useful for measuring chlorine concentration in recreational water bodies in residential and commercial (e.g., hotels, water parks, etc.) facilities. Additionally, such sensors can be useful for measuring concentration of other substances (e.g., dissolved minerals) in fluids in other applications such as water towers, cooling towers and the like to determine the likelihood of fouling.

Figure 1:
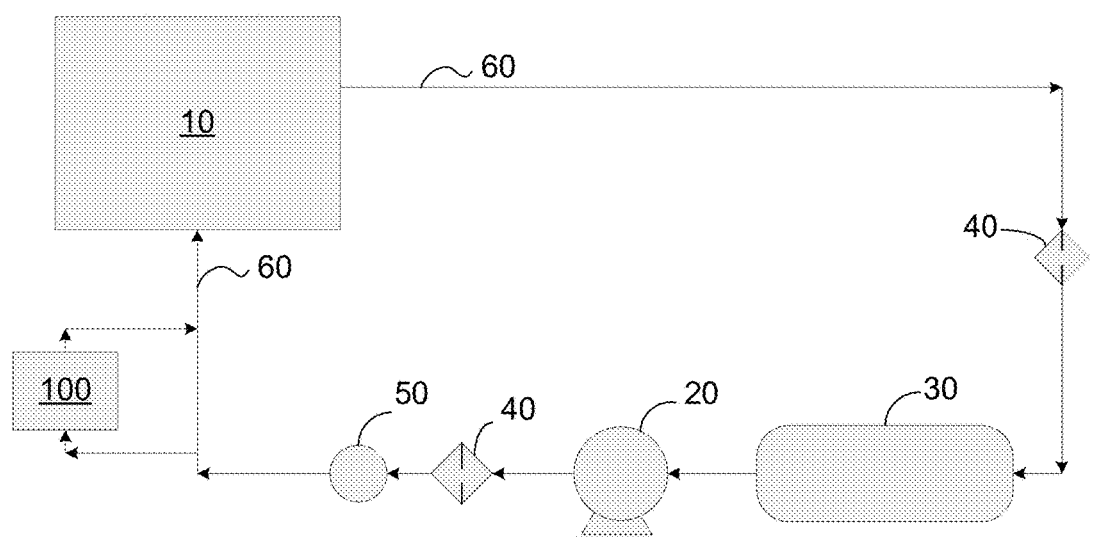
FIG. 1 illustrates an overall schematic of a sensor system for measuring one or more properties of a fluid.

FIG. 1 shows an overall schematic of a water body 10 (e.g., pool or spa) provided with a sensor system 100 according to certain embodiments of the invention. Fluids (e.g., water) can be pumped into the pool by one or more pumps 20 from a reservoir (e.g., a tank) 30. One or more filters 40 can filter any suspended particles or undesirable substances from entering the water body 10. In some cases, one or more flow meters 50 can be provided to measure the flow rate of the fluid flowing out of the pump, through the filter, or at any other portion of the schematic of the main flow line 60 shown in FIG. 1. The pump and tank can be sized to provide and/or maintain a certain flow rate of fluid to the water body 10. In certain exemplary embodiments, the water body 10 can receive between about 10 gallons per minute and about 200 gallons per minute of fluid (e.g., about 100 gallons per minute), or more from the reservoir at a pressure of between about 15 psi and about 30 psi (e.g., at 20 psi).

Figure 2:
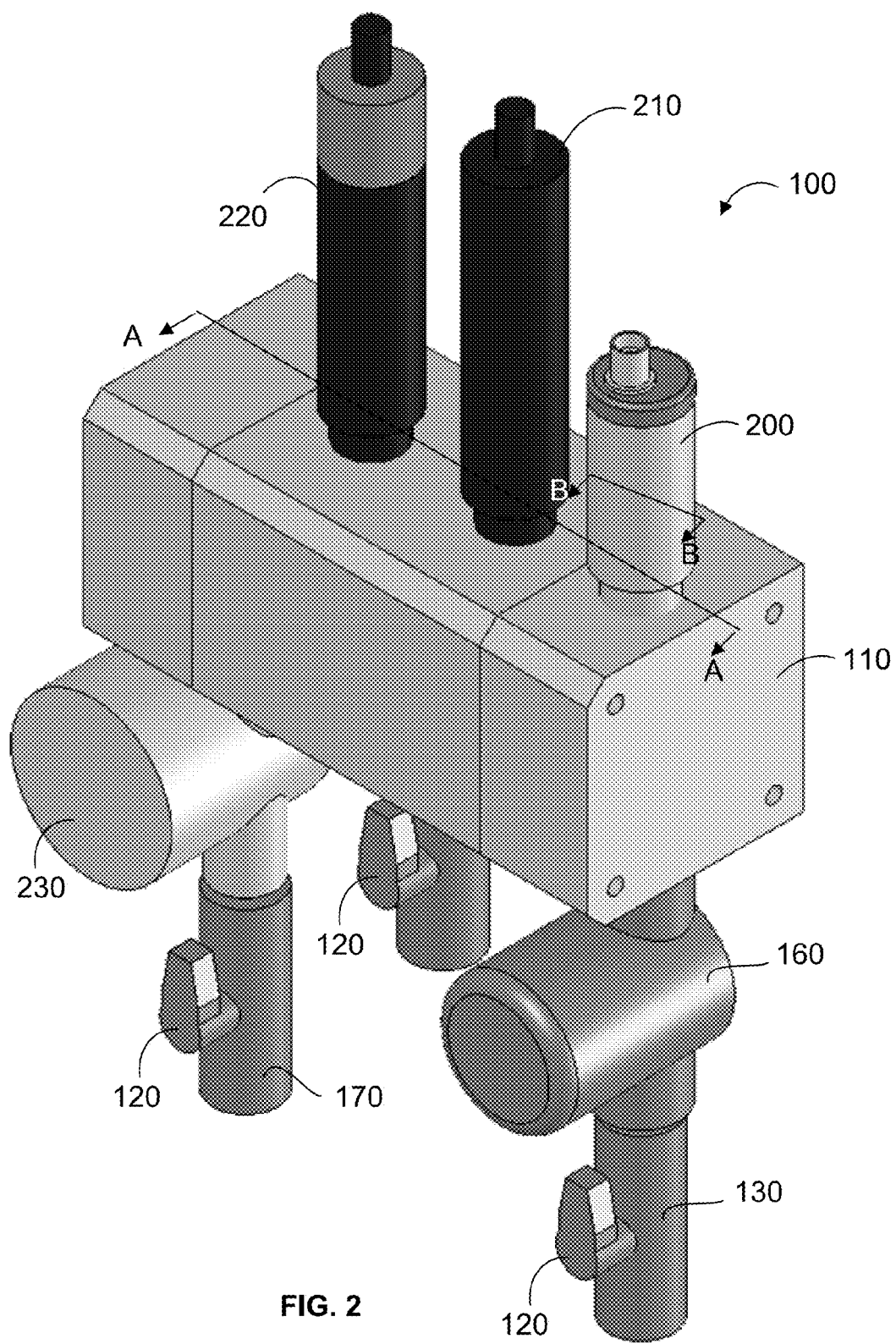
FIG. 2 is a perspective view of a manifold of a sensor system according to certain embodiments of the invention.

With continued reference to FIG. 1, a sensor system 100 can be provided anywhere in the main flow line 60 where a pressure differential occurs to measure certain properties of fluid. In some cases, a fraction of the flow rate of fluid flowing through the main flow line 60 can be tapped and directed into the sensor system 100. As will be described herein and shown in FIG. 2, the sensor system 100 can have a manifold 110. The manifold 110 can have flow passages defined therein for receiving fluid having desired flow characteristics (e.g., flow rate, pressure, turbulence level etc.) from the main flow line 60. The manifold 110 can house one or more sensors for measuring certain properties of the fluid. The manifold 110 can receive fluid at any desired flow rate. For instance, the manifold 110 can receive fluid at a fraction of the flow rate supplied by the pump shown in FIG. 1. In such cases, as shown in FIG. 2, flow control means 120 (e.g., valves, regulators, etc.) can be used to supply water at a manifold flow rate to the manifold 110. Alternatively, the manifold 110 can receive fluid at the entirety of the flow rate supplied by the pump. In some cases, the manifold 110 can receive water at a manifold flow rate. The manifold flow rate can be less than or equal to the flow rate of water into the water body 10. In some exemplary embodiments, the manifold 110 can receive water at a manifold flow rate in the range between about 0.1 gallons per minute and about 10.0 gallons per minute when the flow rate of fluid into the water body 10 is between about 10 gallons per minute and about 200 gallons per minute, or more.

Figure 3:
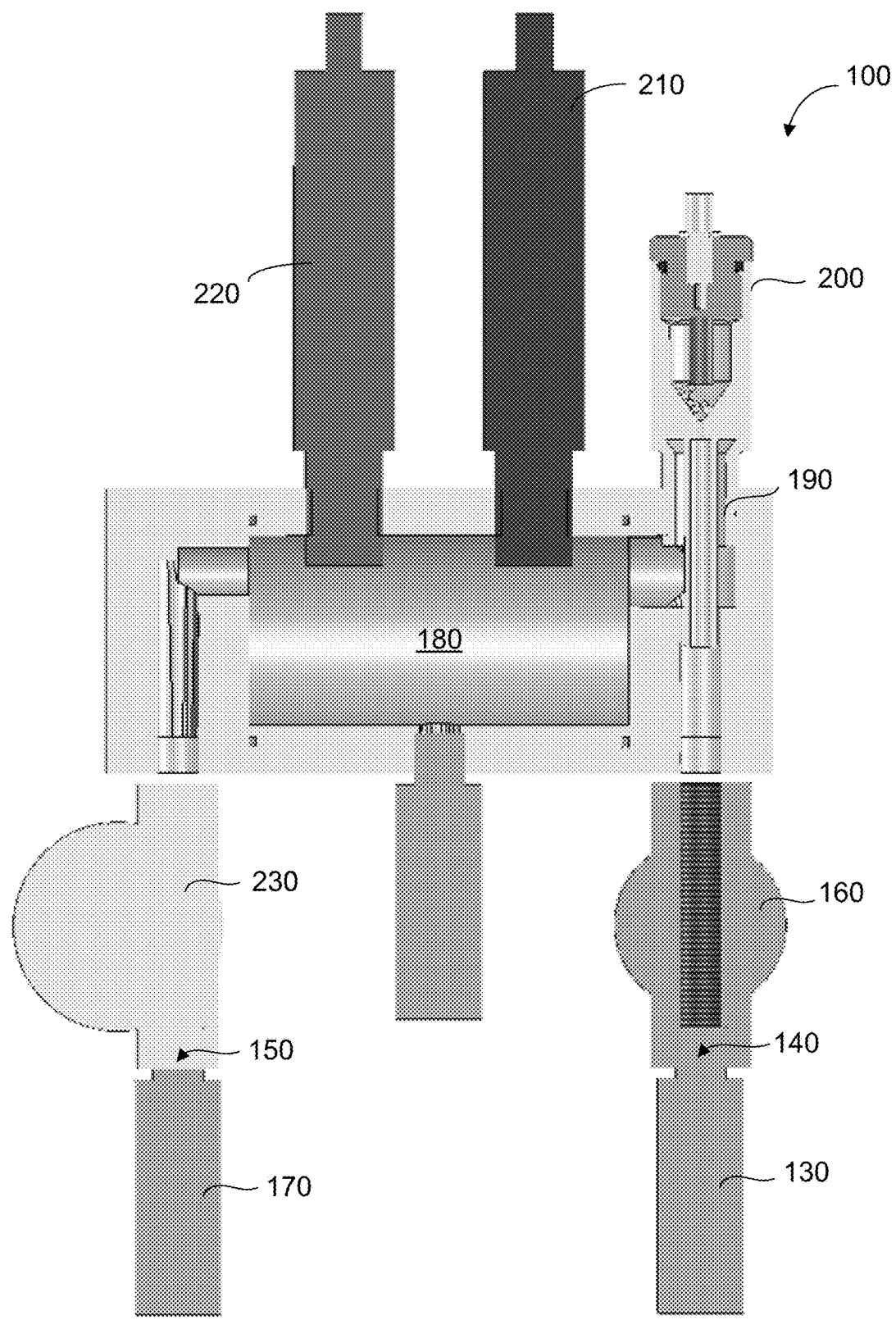
FIG. 3 is a cross-sectional view of the manifold of FIG. 2 taken along the plane A-A.

FIGS. 2 and 3 illustrate a perspective view and a cross-sectional view of the manifold 110 according to an embodiment of the invention. As seen in FIGS. 2 and 3, fluid from any source (not shown) enters a fluid supply line 130 of the manifold 110. In some cases, the source can be the main flow line 60 shown in FIG. 1. As mentioned previously, the manifold 110 can receive fluid at any desired flow rate. Referring back to FIG. 2, the manifold 110 comprises one or more flow control means (e.g., valves, regulators and the like) to regulate and/or control the flow rate of fluid, such that the manifold 110 receives fluid at the desired flow rate. In some cases, the flow control means can be flow restrictor device, ball valve, or small orifice. In some embodiments, the flow characteristics (e.g., flow rate, turbulence, composition of fluid, etc.) can influence the accuracy of measurement of certain properties. In such cases, providing one or more flow control means can allow precise metering of fluid into the manifold 110 so as to eliminate errors in measurement of properties due to turbulence, trapped air bubbles, impurities, or similar effects.

With continued reference to FIG. 3, the manifold 110 comprises a manifold inlet 140 and a manifold outlet 150. The manifold inlet 140 can receive fluid at the desired flow rate. Fluid entering the manifold 110 can pass through a filter 160 housed in a filter housing to eliminate impurities in the fluid to protect one or more sensors housed in the manifold 110 and to facilitate accurate measurement of fluid properties. The filtered fluid may then be directed to one or more flow passages in the manifold 110 that are in fluid communication with one or more sensors for measuring desired fluid properties. The manifold outlet 150 can be in fluid communication with a fluid return line 170 for returning the fluid to the source. As mentioned previously, in some embodiments, the source can be the main flow line 60 seen in FIG. 1. In such cases, fluid can leave the manifold 110 via the manifold outlet 150 and the fluid return line 170, and rejoin the main flow line 60 shown in FIG. 1. In some cases, the manifold inlet 140 receives fluid at a manifold flow rate. In such cases, the manifold outlet 150 can return the fluid to the fluid return line 170, and to the source at the manifold flow rate. In other words, the manifold 110 can be configured to operate in a steady flow configuration with no accumulation of fluid in the manifold 110 over time. However, the manifold 110 can be configured to operate in any desired fashion (e.g., with unsteady flow).

In the embodiments illustrated in FIG. 1, the main flow line 60 is continuously operating to supply fluid to the water body 10 at a nearly constant flow rate. However, the manifold 110 can be used in a variety of other configurations. For instance, the manifold 110 can be fluidly coupled to a tank (e.g., water tank or cooling tower) to measure the properties of a fluid that remains static in the tank. In such cases, a desired rate and/or volume of fluid may be pumped out of the tank and directed toward the fluid supply line 130 of the manifold 110. The manifold 110 may either continuously (e.g., in a steady fashion) or intermittently (e.g., in an unsteady fashion) receive the fluid and measure its properties. The manifold 110 may then return the fluid via the fluid return like back into the tank or to a drain. The particular orientation and configuration of the manifold 110 described herein is for illustrative purposes and does not limit the scope and applicability of the embodiments of the invention disclosed herein.

Referring back to FIG. 3, the manifold 110 comprises a primary flow passage 180 and a secondary flow passage 190, each defined internally in the manifold 110. As seen in FIG. 3, the primary flow passage 180 can be in fluid communication with the fluid supply line 130 and the fluid return line 170. The secondary flow passage 190 can be in fluid communication with the fluid supply line 130. The primary flow passage 180 can receive a first flow rate from the manifold inlet 140, and, the secondary flow passage 190 can receive a second flow rate from the manifold inlet 140. In some cases, the sum of first and second flow rates equal the manifold flow rate. In other words, the primary and the secondary flow passages can be positioned and oriented such that the flow from the fluid supply line 130 splits into two branches, with one branch directed toward the primary flow passage 180 at a first flow rate, and the second branch directed toward the secondary flow passage 190 at a second flow rate. The primary and secondary flow branches may further be positioned or oriented such that the two branches of flow rejoin before leaving the manifold 110. Alternatively, fluid at a second flow rate may enter the secondary flow passage 190, travel towards a probe 200 and then return to the secondary flow passage 190 prior to recombining with fluid directed toward the primary flow passage 180.

As mentioned previously, the primary and secondary flow passages can be positioned and oriented such that flow from the fluid supply line 130 has the desired flow characteristics such as flow rate, turbulence levels, lack of trapped particles or bubbles and the like. In some exemplary embodiments such as those illustrated in FIG. 3, the primary flow passage 180 and the secondary flow passage 190 are oriented perpendicularly to each other. However, any desired orientation can be used without loss of functionality. Additionally, the primary flow passage 180 is of larger cross-sectional area than the secondary flow passage 190. Further, the orientation and cross-sectional area of the primary and the secondary passages can be such that the first and second flow rates entering the primary and secondary passages are at a desired value. For instance, the second flow rate can be between about 1% and about 50% of the first flow rate. Further, the desired first and second flow rates can also be maintained by pressurizing the fluid by any known means (e.g. venturis, pumps, and the like) to maintain a desired (e.g., positive) pressure difference in the primary and/or secondary flow passages.

As seen in FIG. 3, the manifold 110 comprises one or more sensors in fluid communication with the primary flow passage 180 or the secondary flow passage 190 for measuring one or more fluid properties. In many cases, fluid properties may not vary in water bodies such as pools. However, in other cases, fluid properties may vary and any change in one fluid property (e.g., pH or temperature) may affect other fluid properties (e.g., concentration of chlorine). In order to accurately measure fluid properties which may be influenced by other fluid properties, the manifold 110 includes a plurality of sensors for measuring a number of fluid properties. In some cases, the manifold 110 includes at least one of a concentration sensor (e.g., amperometric probe 200 shown in FIG. 3), pH sensor 210, a conductivity sensor, a temperature sensor 220 and a flow meter 230. In the embodiment illustrated in FIG. 3, the chlorine concentration sensor (e.g., amperometric probe 200) is in fluid communication with the secondary flow passage 190 while the pH, temperature sensors 210, 220 and flow meter 230 are in fluid communication with the primary flow passage 180. The pH sensor 210, conductivity, temperature sensor 220 and flow meter 230 can be of any known type. In some cases, the sensors 210, 220, 230 can measure at least one of concentration of a substance (e.g., chlorine), pH, conductivity, temperature and volumetric flow rate of the fluid flowing through the manifold 110. Additionally, the sensors 210, 220, 230 are adapted to simultaneously measure at least two of pH, conductivity, temperature and volumetric flow rate of the fluid flowing through the manifold 110. In some embodiments, the sensor system 100 can be a part of a feedback control loop (not shown), wherein the sensor system 100 can provide one or more measured properties (e.g., chlorine concentration or pH) as an input into the feedback control loop. The feedback control loop may have a controller (e.g., a microcontroller or a computer program) that can then decide whether to add one or more substances (e.g., chlorine) to bring a measured property (e.g., chlorine concentration, pH, etc.) to a desired level.

Figure 4:
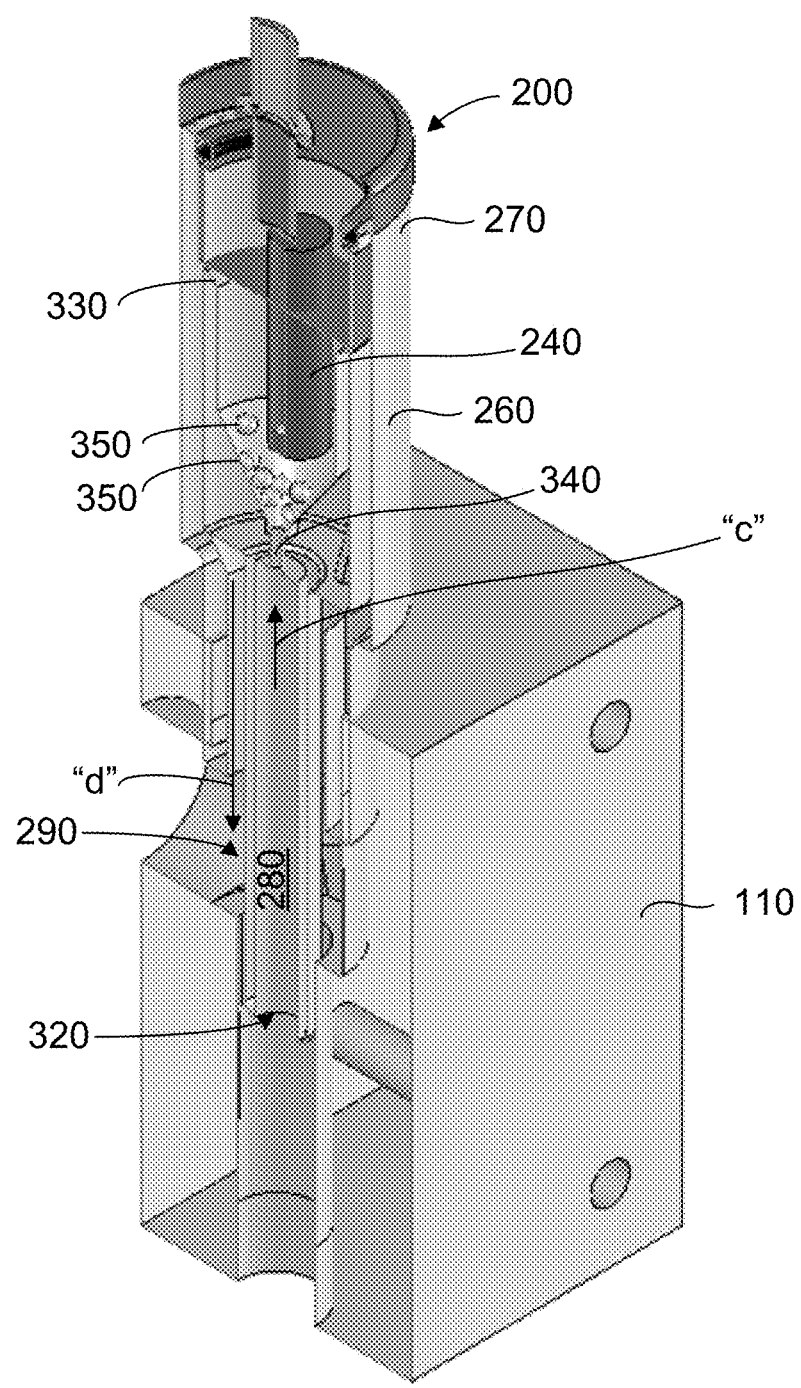
FIG. 4 is a portion of the cross-sectional view of the manifold of FIG. 2 taken along the plane B-B.
Figure 5:
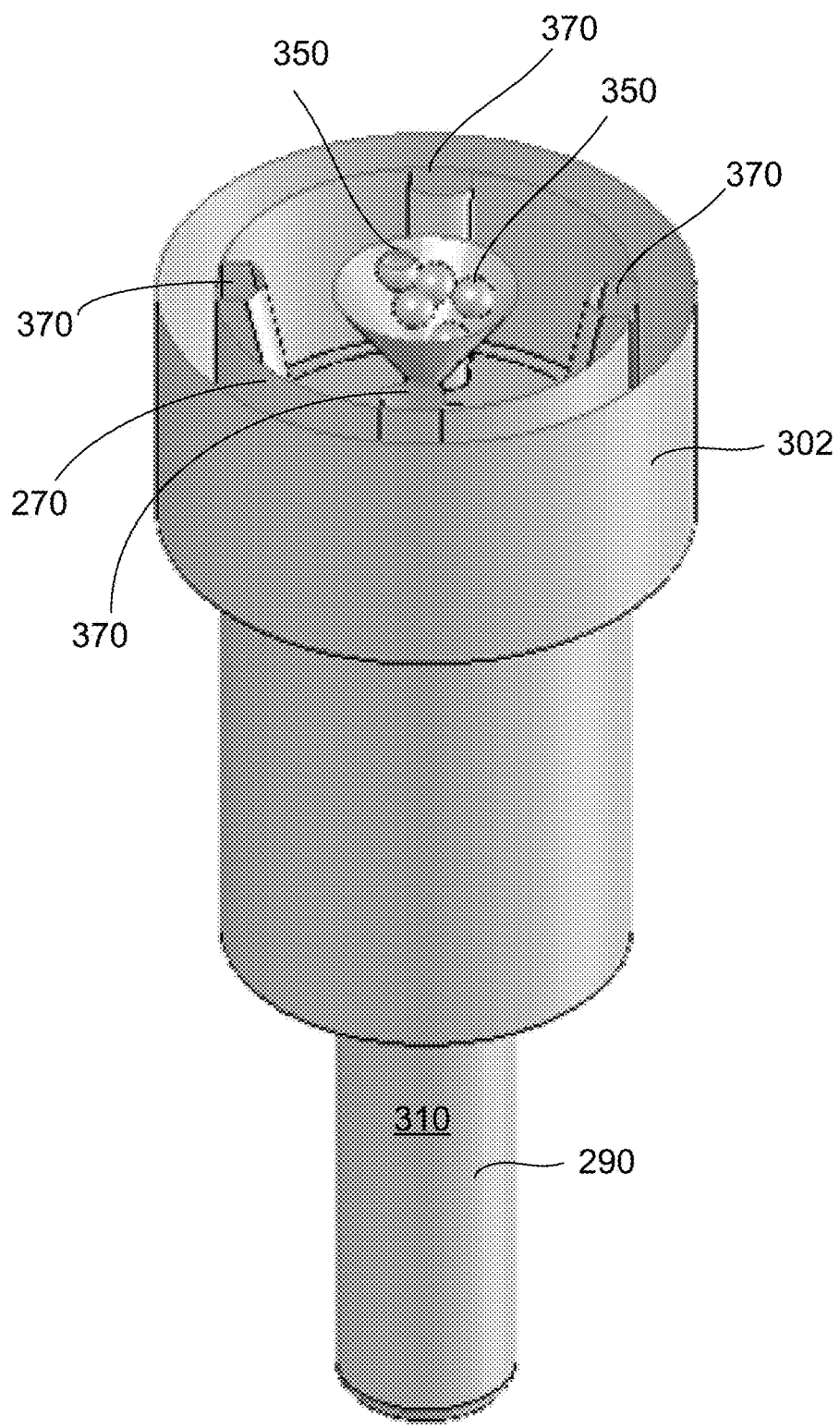
FIG. 5 is a perspective view of a portion of an amperometric probe according to certain embodiments of the invention.

Referring now to FIGS. 4 and 5, the manifold 110 comprises a concentration sensor 200 for measuring concentration of a substance (e.g., chlorine). In some embodiments, the concentration can be an amperometric probe. The general principles of operation of amperometric probes for measuring concentration of substances (e.g., chlorine) are well-known in the art and a description thereof is omitted for clarity. The amperometric probe 200 can be operated in a bias voltage mode or a galvanic mode. As seen in the plan view of FIG. 6, the probe 200 comprises a plurality of electrodes. In the illustrated embodiment, the probe 200 comprises an anode 240 and a cathode 250 housed at an upper portion 260 thereof. The upper portion can be electrically isolated from the surroundings and capped off (e.g., with a plastic cap press-fitted or threaded to the probe). The electrodes 240, 250 can be connected to a power supply (not shown) to provide a bias voltage across the electrodes 240, 250. The electrodes 240, 250 are illustrated as being cylindrical in shape, but can be of any shape. In the embodiments illustrated herein, the anode 240 is made of copper and has a diameter of between about 3 mm and about 12 mm. The anode 240 and the cathode 250 can be spaced apart by a distance of between about 1 mm and about 20 mm (e.g., about 5 mm). The electrodes 240, 250 are in fluid communication with the fluid entering the probe 200. The electrodes 240, 250 generate a current that is proportional to the concentration of a specific substance (e.g., chlorine). The cathode 250 can be of any suitable metal or alloy, and in the illustrated embodiment, is made of platinum. Embodiments of the probe 200 described herein can advantageously facilitate the use of copper anode 240 of a lower diameter than typical amperometric probes while maintaining a probe 200 life of between about three years and about five years of continuous operation of the probe 200. Such embodiments can be beneficial if the electrodes (e.g., copper anode) dissolve during use.

Referring back to FIG. 4, the probe 200 can be positioned in fluid communication with the secondary flow passage 190. The probe 200 comprises a probe body 270 defining a hollow portion 280. While it is sufficient for the probe 200 to be in fluid communication with the secondary flow passage 190, in some cases, the probe 200 is physically connected to the secondary flow passage 190. For instance, the probe body 270 can have a stem 290 below the upper portion 260 thereof (e.g., vertically below the upper portion 260 which houses the electrodes 240, 250), which can be inserted into the secondary flow passage 190. While the illustrated embodiments show the stem 290 having a cross-sectional area less than that of the upper portion 260 of the probe body 270, in other embodiments, the stem 290 can have a cross-sectional area greater than or equal to that of the upper portion 260 of the probe body 270. For instance, the probe body and the stem can be cylindrical in shape having a diameter of between about 15 mm and about 25 mm, and between about 1 mm and about 10 mm respectively. In such cases, the upper portion 260 has a length of between of about 10 mm and about 50 mm (e.g., about 25 mm), and the stem 290 can have a length between about 20 mm and about 80 mm (e.g., about 55 mm). Such embodiments allow the electrodes 240, 250 to extend a distance of between about 10 mm and about 20 mm into the upper portion 260 and be in fluid communication with the incoming fluid from the secondary flow passage 190. In some cases the stem 290 of the probe body 270 can have the hollow portion 280, via which the fluid can enter the probe 200. The hollow portion can have an internal diameter of between about 1 mm and about 10 mm (e.g., about 6 mm). As shown in the illustrated embodiments, the stem 290 can be placed coaxially with the secondary flow passage 190, defining an annular gap 300 between an outer surface 310 of the stem 290 and the walls of the secondary flow passage 190. However, the probe body 270 can also be offset from the secondary flow passage 190. The probe body 270 can be configured (e.g., shaped and/or oriented in the secondary flow passage 190) such that the second flow rate of fluid enters the probe 200 and is directed toward the electrodes 240, 250 for measuring the concentration of a substance with a desired accuracy. In some cases, the probe body and the electrodes can be enclosed in an outer casing with a cap and inserted into passages of the manifold 110 (e.g., secondary flow passage 190). For instance, the outer casing can have a threaded, press-fitted, fastened, or bonded engagement with a passage (e.g., secondary flow passage 190) of the manifold 110.

Figure 6:
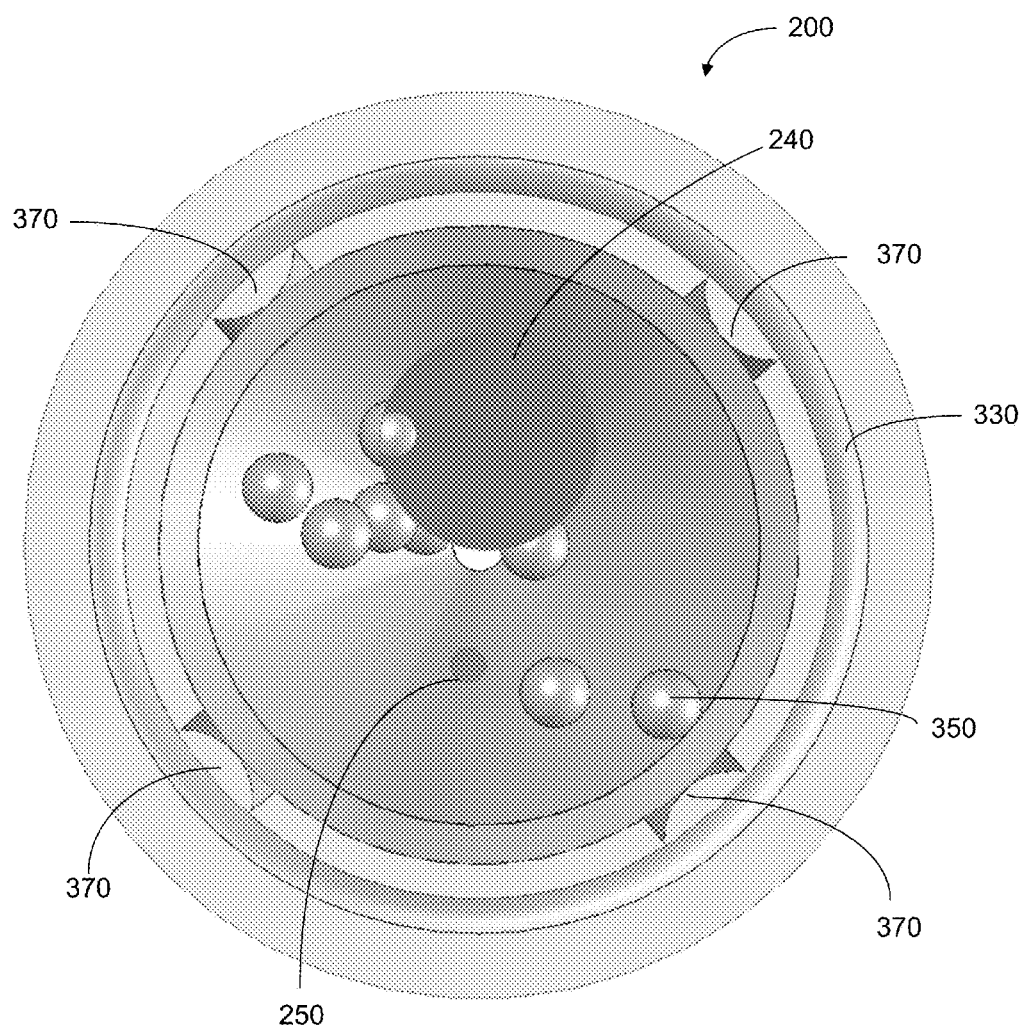
FIG. 6 is a top plan view of an amperometric probe shown in FIG. 5.

With continued reference to FIG. 4, the probe body 270 can have a first end 320 and a second end 330 opposite the first end 320. The hollow portion 280 of the stem 290 can receive the second flow rate proximal to the first end 320. The probe body 270 can be shaped and oriented to direct the fluid flowing at the second flow rate toward the second end 330 of the probe body 270, and from the second end 330 of the probe body 270 back toward the secondary flow passage 190. As is seen in FIGS. 4 and 6, the second end 330 is proximal to the electrodes 240, 250. In some cases, the probe 200 can include a nozzle 340 in fluid communication with the hollow portion 280 of the stem 290. As perhaps best seen in the close-up view of FIG. 7, the nozzle 340 can be coaxial with the hollow portion 280 of the stem 290 and the secondary flow passage 190. The nozzle 340 can be shaped such that it generates a jet of fluid flowing from the secondary flow passage 190, and directs the jet toward the second end 330 of the probe body 270. The nozzle 340 can be shaped such that it has a cross-sectional area less than the cross-sectional area of the hollow portion 280 of the stem 290, thereby accelerating the fluid flowing through the hollow portion 280 of the stem 290. In some embodiments, the nozzle 340 has a diameter (e.g., at or proximate to the nozzle exit 360) of between about 1 millimeter and about 3 millimeter. In certain embodiments, the nozzle 340 is adapted to suppress turbulence and/or air bubbles in the incoming fluid (e.g., fluid flowing from the secondary flow passage 190).

Figure 7:
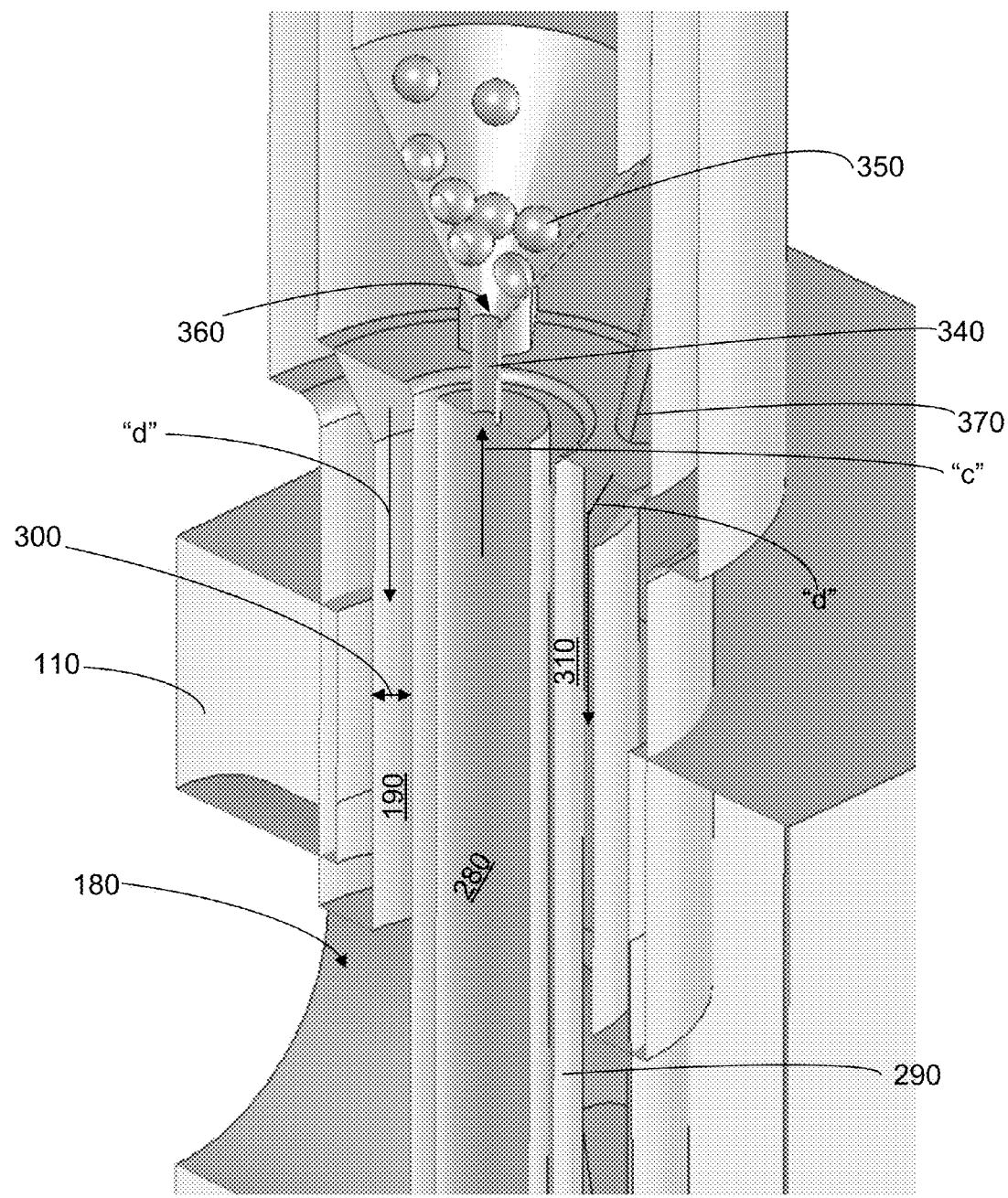
FIG. 7 is a perspective view of a portion of an amperometric probe taken along the plane B-B shown in FIG. 5.

With continued reference to FIG. 7, the fluid enters the upper portion 260 of the probe body 270 via the hollow portion 280 of the stem 290, passes through the nozzle 340 and is accelerated to form a jet therein, and is directed toward the second end 330 of the probe body 270, proximal to the electrodes 240, 250. The electrodes 240, 250 generate a current in response to flow characteristics and concentration of a substance (e.g., chlorine). The fluid may then be directed (e.g., by a pressure difference) to flow out of the probe body 270 and back into the secondary flow passage 190. As seen in FIG. 7, and described previously, the probe body 270 and the walls of the secondary flow passage 190 define an annular gap 300 therebetween. The fluid from the second end 330 can be directed into the annular gap 300 between the probe body 270 (e.g., stem 290) and the walls of the secondary flow passage 190. In some embodiments, the primary flow passage 180 and the secondary flow passage 190 are fluidly coupled such that the fluid from the second end 330 of the probe body 270 flowing through the secondary flow passage 190 mixes with the fluid directed toward the primary flow passage 180. In such cases, the fluid from the secondary flow passage 190 can be directed toward the primary flow passage 180 by any known means (e.g., pressure differential, gravity and the like). Once mixed, the fluid can flow through the primary flow passage 180 and can remain in fluid communication with one or more sensors for measuring fluid properties such as pH, conductivity, temperature and flow rate. The fluid may then be directed (e.g., by creating a pressure difference) out of the manifold 110 and join the main flow line 60 as described previously.

As seen in FIG. 7, the probe 200 can comprise a plurality of beads 350 positioned proximal to the nozzle exit 360. The beads 350 can be configured to remain seated against the nozzle exit 360 when there is no flow through the nozzle 340, and can be lifted from their seated position when fluid flows out of the nozzle 340. In some cases, the beads 350 can be made of glass, although other materials (e.g., polymers, ceramics or other electrically insulating materials) are also contemplated. The beads 350 are spherical in shape in the illustrated embodiment, although they can be of any shape or size and be lifted a desired distance in response to the flow from the nozzle 340 directed toward the second end 330 of the probe body 270. As is generally known, the beads 350 prevent corrosion (e.g., due to fouling) of the electrodes 240, 250. Particularly with reference to the embodiments illustrated in FIG. 7, the beads 350 may be lifted vertically upward from the nozzle exit 360 due to the jet of fluid from the nozzle 340 impacting against the beads 350. The beads 350 may move proximal to the electrodes 240, 250 (e.g., copper anode 240) and rub and/or polish the anode 240 to remove any scaling, sediment deposits, or other means that corrode the copper anode 240. The beads 350 can be of a size sufficient to effectively contact and scrape the anode 240 without blocking the fluid flowing out of the nozzle 340. Likewise any number of beads 350 that allow a sufficient quantity of flow and/or at a desired flow rate to reach the electrodes 240, 250 but suppress turbulence or trapped air bubbles can be used. Such embodiments can prevent clogging of the probe 200 due to sediments or deposits, and increase the operational life of the probe 200. Additionally, reduced clogging may result in better accuracy of concentration measurement.

Figures 8A, 8B:
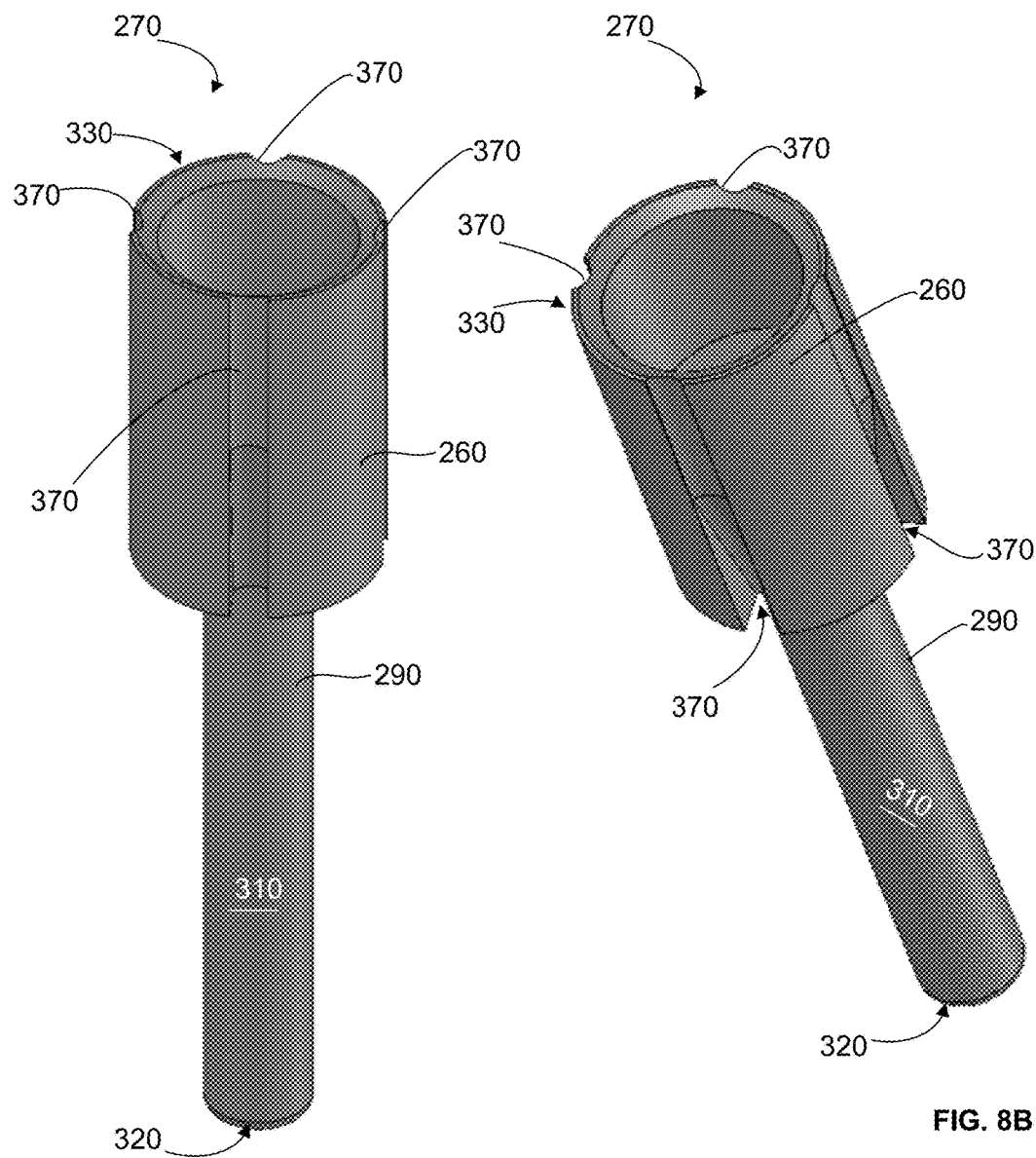
FIGS. 8A and 8B are perspective views of an exterior portion of the amperometric probe of FIG. 5.

Referring now to FIGS. 8A and 8B, a portion of an outer surface 310 of the probe body 270 has a plurality of flutes 370 defined therein to direct fluid flowing from the second end 330 (e.g., near an upper portion 260 of the probe body 270) back into the secondary flow passage 190. Referring back to FIG. 7, the annular gap 300 is in fluid communication with the primary flow passage 180, so that the fluid directed by the flutes 370 into the annulus is further directed into the primary flow passage 180. In some cases, the flow entering and/or leaving the nozzle 340 is oriented along a first direction "c" (e.g., vertically upward direction) shown in FIG. 7, and the flow from the flutes 370 and into the second any flow passage is along a second direction "d", wherein the first direction is opposite to the second direction. With reference to FIGS. 8A and 8B, the flutes 370 can be shaped and oriented to direct fluid from the second end 330 to flow along the flutes 370 into the annulus between the nozzle 340 and the probe body 270. For instance, the flutes 370 can be tapered, angled or slotted for at least a portion of the length of an upper portion 260 of the probe body 270 to direct the flow from the second end 330 into the annulus. In the illustrated embodiments shown in FIGS. 8A and 8B, the flutes 370 taper radially inwardly toward the axis of the probe 200. In the embodiments shown in FIGS. 8A and 8B, four flutes 370 are positioned symmetrically (e.g., about the circumference) on the outer surface 310 of the probe body 270. However, any number of flutes 370 can be used that direct flow toward the annulus can be used. Other orientations and/or shapes of the flutes 370 are also contemplated.

In certain embodiments, the probe body 270 can be configured to facilitate visual inspection of flow through the probe body 270. An operator can ensure by visually inspecting the probe body 270 that a continuous stream of fluid contacts the electrodes 240, 250 and that the beads 350 are in motion to clean the electrodes 240, 250. In one example, the probe body 270 is made of a polymer transparent to visible light to facilitate visual inspection of flow through the probe 200. For instance, the probe body 270 can be made of polyvinyl chloride (PVC) transparent to visible light. Alternatively, in another example, a portion of the probe body 270 can have a transparent window (e.g., made of glass and/or transparent polymers such as PVC, not shown) to allow an operator to inspect the condition of the probe 200. For instance, only a portion of the probe body 270 can be transparent to allow an operator to visualize that the passages (e.g., through the nozzle and toward the electrodes) are not clogged, and to inspect the condition of the electrodes (e.g., anode). Additionally, the beads 350 may have a non-clear outer surface 310 (e.g., opaque and/or having a color other than white or clear) to facilitate inspection of movement of the beads 350. Other visual aids may also be incorporated into such embodiments to inspect the condition of the probe 200.

In one embodiment of a method of measuring fluid properties with the sensor system 100, and with reference to FIGS. 4 and 8A-8B, the fluid first enters the hollow portion 280 of the stem 290 of the probe body 270 at the first end 320. The fluid travels vertically upwardly along direction "c" toward the nozzle 340. The nozzle 340 generates a jet to lift the plurality of beads 350 further vertically upwardly from the nozzle exit 360 and toward the electrodes 240, 250 and prevent sediments deposition or corrosion from occurring at the anode 240 and/or cathode 250. The fluid may then continue flowing further upwardly until it reaches the upper edge of the probe body 270, and is directed into the flutes 370 positioned on an outer surface 310 along the circumference of the upper portion 260 of the probe body 270. The flutes 370 may direct the fluid toward the secondary flow passage 190 in a downwardly direction "d" into the annulus between the probe body 270 and the walls of the secondary flow passage 190. As the annulus is in fluid communication with the primary flow passage 180, fluid flowing downwardly from the flutes 370 into the annulus is further directed (e.g., due to a pressure differential generated due to a pressurizing means such as pumps, venturi or gravity-induced flow) into the primary flow passage 180. The fluid may then contact one or more sensors housed in fluid communication. The sensor(s) may measure one or more fluid properties such as pH, temperature, flow rate and the like. The fluid can then flow out of the manifold 110 via the manifold outlet 150 and the fluid return line 170 to rejoin the main flow line 60 shown in FIG. 1.

A number of optional features may be incorporated into the sensor system and method described herein. For instance, the sensor system can be a part of a feedback control system wherein the measured fluid properties can be sent to a microcontroller to make one or more decisions. For instance, based on the measured pH or chlorine concentration, the microcontroller can determine the levels of pH or chlorine to be lower than a desired level, and a suitable dosage of additives (e.g., disinfectant, sanitizer) can be added to the fluid to bring the levels of pH or chlorine to a desired value. Additionally, the sensor system can be interfaced (e.g., via a software program) with an operator allowing the operator to record and/or monitor various fluid properties over time. Additionally, the sensor system can alert the operator if any of the measured fluid properties are out of a desired range.

Amperometric sensors according to embodiments of the invention ensure accurate measurement of chlorine concentration due to improved fluid flow design. Embodiments of the probe disclosed herein ensure a steady flow of fluid reaching the electrodes, thereby facilitating a steady signal output from the electrodes representative of chlorine concentration. Additionally, the flow passages can be shaped, sized and oriented to allow optimal flow rates of fluid reaching the electrodes, thereby ensuring that a signal output of sufficient magnitude can be generated by the electrodes. The flow passages also suppress turbulence and minimize any trapped air bubbles to improve signal output of the amperometric probe.

Certain embodiments of the sensor system offer improved fluid flow design in the sensor system that reduces clogging and provides optimal flow rates through various sensors in the sensor system. Embodiments of the invention also facilitate the use of larger electrodes than known designs, and longer operational life of the probe. Sensor systems according to certain embodiments of the invention have lower manufacturing costs than typical sensor systems. When incorporated into chemical dispensing systems for recreational swimming pools, spas and water parks, sensor systems according to certain embodiments of the invention provide improved regulation and control of pH and chlorine levels in recreational water bodies such as pools, spas and water towers.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention.

What is claimed is:

1. A sensor system for measuring chlorine concentration in water, comprising:
   a manifold, comprising:
      a manifold inlet, in fluid communication with a fluid supply line, for receiving a manifold flow rate from a source to the manifold,
      a manifold outlet, in fluid communication with a fluid return line, for returning the manifold flow rate from the manifold to the source,
      a primary flow passage defined in the manifold and in fluid communication with the fluid supply line and the fluid return line, the primary flow passage adapted to receive a first flow rate from the manifold inlet, and
      a secondary flow passage defined in the manifold, the secondary flow passage adapted to receive a second flow rate from the manifold inlet, the second flow rate being substantially smaller than the first flow rate;
   one or more sensors in fluid communication with the primary flow passage for measuring one or more fluid properties of the fluid flowing through the primary flow passage; and a probe for measuring chlorine concentration, the probe being positioned in fluid communication with the secondary flow passage, the probe comprising:
  a probe body defining a hollow portion, the probe body having a first end and a second end opposite to the first end, the hollow portion adapted to receive the second flow rate proximal to the first end, the probe body shaped and oriented to direct the second flow rate toward the second end of the probe body, and from the second end of the probe body toward the secondary flow passage,
  a plurality of electrodes positioned in the hollow portion proximal to the second end and contacting the fluid in the hollow portion, the electrodes adapted to generate a current in response to the concentration of chlorine present in the fluid.

2. The sensor system of claim 1, wherein the manifold flow rate equals the sum of the first flow rate flowing through the primary flow passage and the second flow rate flowing through the secondary flow passage.

3. The sensor system of claim 1, wherein the primary flow passage and the secondary flow passage are oriented such that the fluid from the second end of the probe body flowing through the secondary flow passage mixes with the fluid directed toward the primary flow passage.

4. The sensor system of claim 1, wherein the probe body is coaxial with the secondary flow passage.

5. The sensor system of claim 4, further comprising a nozzle in fluid communication with the hollow portion of the probe body, the nozzle being coaxial with the probe body and the secondary flow passage, the nozzle being shaped such that it generates a jet of fluid flowing through the hollow portion, and directs the jet of fluid toward the second end of the probe body.

6. The sensor system of claim 1, wherein the primary flow passage and the secondary flow passage are oriented perpendicular to each other.

7. The sensor system of claim 1, wherein the primary flow passage is of larger cross-sectional area than the secondary flow passage.

8. The sensor system of claim 1, wherein the electrodes include a platinum cathode and a copper anode, the platinum cathode and the copper anode extending into the hollow portion from the second end toward the first end.

9. The sensor system of claim 1, wherein the one or more sensors include at least one of a pH sensor, a temperature sensor and a flow meter.

10. The sensor system of claim 1, wherein the one or more sensors are adapted to measure at least one of pH, conductivity, temperature, and volumetric flow rate of the fluid flowing through the manifold.

11. The sensor system of claim 10, wherein the one or more sensors are adapted to simultaneously measure at least two of pH, conductivity, temperature and volumetric flow rate of the fluid flowing through the manifold.

12. A sensor probe to be used in a sensor system for measuring concentration of chlorine in a fluid, the fluid flowing through a plurality of passages defined in the sensor system, the probe comprising:
  a pair of electrodes for measuring concentration of chlorine in the fluid based on the flow of electric current;
  a probe body having
    a hollow portion in fluid communication with a first flow passage of the sensor system,
    a first end proximal to the first flow passage, and
    a second end distal to the first end;
  a nozzle in fluid communication with the hollow portion of the probe body, the nozzle being coaxial with the hollow portion of the probe body, the nozzle receiving fluid from the hollow portion, the nozzle being shaped to direct the fluid from the hollow portion toward the second end;
  an annulus that generally surrounds the nozzle;
  a portion of an outer surface of the probe body having a plurality of flutes defined therein, the flutes being shaped and oriented to direct fluid from the second end to flow along the flutes into the annulus.

13. The sensor probe of claim 12, wherein the annulus is in fluid communication with a second flow passage of the sensor system, such that the fluid directed by the flutes into the annulus is further directed into the second flow passage of the sensor system.

14. The sensor probe of claim 13, wherein the flow from the first flow passage to the nozzle is oriented along a first direction and the flow from the flutes and into the second flow passage is along a second direction, wherein the first direction is opposite to the second direction.

15. The sensor probe of claim 12, wherein the nozzle is adapted to suppress turbulence in the fluid flowing from the first flow passage and toward the second end of the nozzle.

16. The sensor probe of claim 15, further comprising a plurality of glass beads positioned in proximal to the nozzle, the plurality of glass beads being adapted to move in response to the fluid directed toward the second end by the nozzle.

17. The sensor probe of claim 12, wherein the probe body is made of a polymer transparent to visible light.

* * * * *